US00PP18174P2

(12) United States Plant Patent
Korlipara

(10) Patent No.: US PP18,174 P2
(45) Date of Patent: Oct. 30, 2007

(54) ***VERBASCUM* PLANT NAMED 'LEMON SORBET'**

(50) Latin Name: ***Verbascum* hybrid (*V. phoeniceum*×*dumulosum*)×*V.* sp. 'Electric Yellow')**
Varietal Denomination: Lemon Sorbet

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 11/444,653

(22) Filed: May 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Verbascum* plant characterized by numerous yellow flowers on numerous upright flowering stems, and excellent vigor.

1 Drawing Sheet

Botanical classification: *Verbascum* hybrid ((*V. phoeniceum*×*dumulosum*)×*V.* sp. 'Electric Yellow').

Variety denomination: 'Lemon Sorbet'.

Cross reference to: co-pending application for *Verbascum* 'Sunshine Spires' (U.S. Plant Pat. No. 17,190).

The present invention relates to a new and distinct cultivar of *Verbascum* hybrid, and given the cultivar name 'Lemon Sorbet'. *Verbascum* is in the family Scrophulariaceae.

This new cultivar originated as a controlled cross in a cultivated area between *Verbascum* 'Jackie' (an unpatented plant) as the seed parent and *Verbascum* sp. 'Electric Yellow' (an unpatented plant) as the pollen parent. *Verbascum* 'Jackie' is a cross between *Verbascum phoeniceum* and *Verbascum dumulosum.*

This new *Verbascum* hybrid is unique in its large yellow colored flowers combined with its multiple flowering stems.

This plant is characterized by the following:

1. Large yellow flowers.
2. Numerous upright, branching flowering stems.
3. Large, soft leaves.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of a one year old *Verbascum* 'Lemon Sorbet' grown in the ground in the trial field in bloom in summer.

DETAILED PLANT DESCRIPTION

The following is a detailed description of the new *Verbascum* selection based on observations of one-year-one specimens grown in the ground in full sun under typical outdoor conditions in Canby, Oreg. Canby is Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Form.*—Clumping basal rosette.
*Hardiness.*—U.S.D.A. Hardiness Zones 6–9.
*Size.*—26 cm tall and 42 cm wide, not including inflorescence.
*Vigor.*—Excellent.
*Roots.*—Fibrous, with many downward growing and few laterals, ivory in color, Yellow White 158D. Roots develop slowly from cuttings from the crown.

Leaf:

*Type.*—Simple.
*Arrangement.*—Basal.
*Shape.*—Ovate.
*Blade size.*—Grows to 24 cm long and 12 cm wide.
*Venation.*—Pinnate.
*Margins.*—Irregularly crenate overall, slightly undulate.
*Apex.*—Acute.
*Base.*—Cuneate.
*Texture.*—Leathery, fuzzy.
*Surface.*—Stellate pubescent on both sides.
*Petiole.*—Length — grows to 5 cm. Width — grows to 14 mm. Surface — stellate pubescent. Color — Yellow Green 145C.
*Leaf color.*—Top side — Green 146B with lighter main vein, Yellow Green 145C. Bottom side — Yellow Green 147C.

Inflorescence:

*Type.*—Panicle.
*Total panicle size.*—10 cm wide and 30 cm high (where flowers are).
*Number of panicles per plant.*—5 to 8.

*Cauline leaves.*—Many in 3 cm internodes, 3 to 24 cm long and 3 to 8.5 cm wide (including petioles), ovate, with tips acute to acuminate, margins crenate, stellate pubescent, color the same as the basal leaves.

*Flower number.*—Count of 200 flowers on one panicle.

*Peduncle.*—Height — grows to 60 cm. Diameter — 13 mm near base. Surface — stellate pubescent. Color — Yellow Green 145C.

*Pedicel.*—Length — grows to 15 mm. Surface — stellate pubescent. Color — Yellow Green 145C.

*Bloom time.*—May through August in Canby, Oreg.

Flower bud:

*Size.*—12 mm wide and 11 mm deep.

*Description.*—Pentagonal cushion.

*Surface.*—Stellate pubescent.

*Color.*—Yellow Orange 17A tinged with Greyed Orange 163A.

Flower:

*Type.*—Perfect, complete, irregular.

*Shape.*—Rotate, irregular, short tubular.

*Size.*—3 cm wide and 1 cm deep including stamens.

*Color.*—Yellow Orange 14A on both sides, tinged with Yellow Orange 22A. The center of the inside of the corolla is eyed, Greyed Purple 183B.

*Corolla.*—Lobe number — 5. Description — margins entire, apex obtuse. Size — 4 cm wide and 1.5 cm deep, somewhat cupped. Surface — glabrous on both sides.

*Calyx.*—Sepal number — 5. Size — 14 mm wide and 3 mm deep. Surface — stellate pubescent and glandular on back side, glabrous inside. Color — Yellow Green 146B on both sides.

*Stamens.*—Number — 5. Filaments — 8 mm long, lower two stamens Yellow 11A on bottom half and lightly bearded Violet 83A above, upper three stamens are Orange 24A on the bottom half and beaded Violet 83A above. Anthers — Kidney shaped. Orange 24A. Pollen — Orange 28A.

*Pistil.*—12 mm long, ovary is 2.5 mm long and Yellow Green 146C, style is 9 mm. long and Yellow Green 147D, stigma is Yellow Green 147B.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

Compared to *Verbascum* 'Electric Yellow' (unpatented), the pollen parent, *Verbascum* 'Lemon Sorbet' has smaller flowers, much more branching, and is much shorter.

Compared to *Verbascum* 'Jackie' (unpatented), the seed parent, *Verbascum* 'Lemon Sorbet' has yellow flowers rather than soft pink.

Compared to *Verbascum* 'Sunshine Spires' (U.S. Plant Pat. No. 17,190), a sibling, the flower color of this new variety is a deeper yellow.

I claim:

1. A new and distinct *Verbascum* plant as herein illustrated and described.

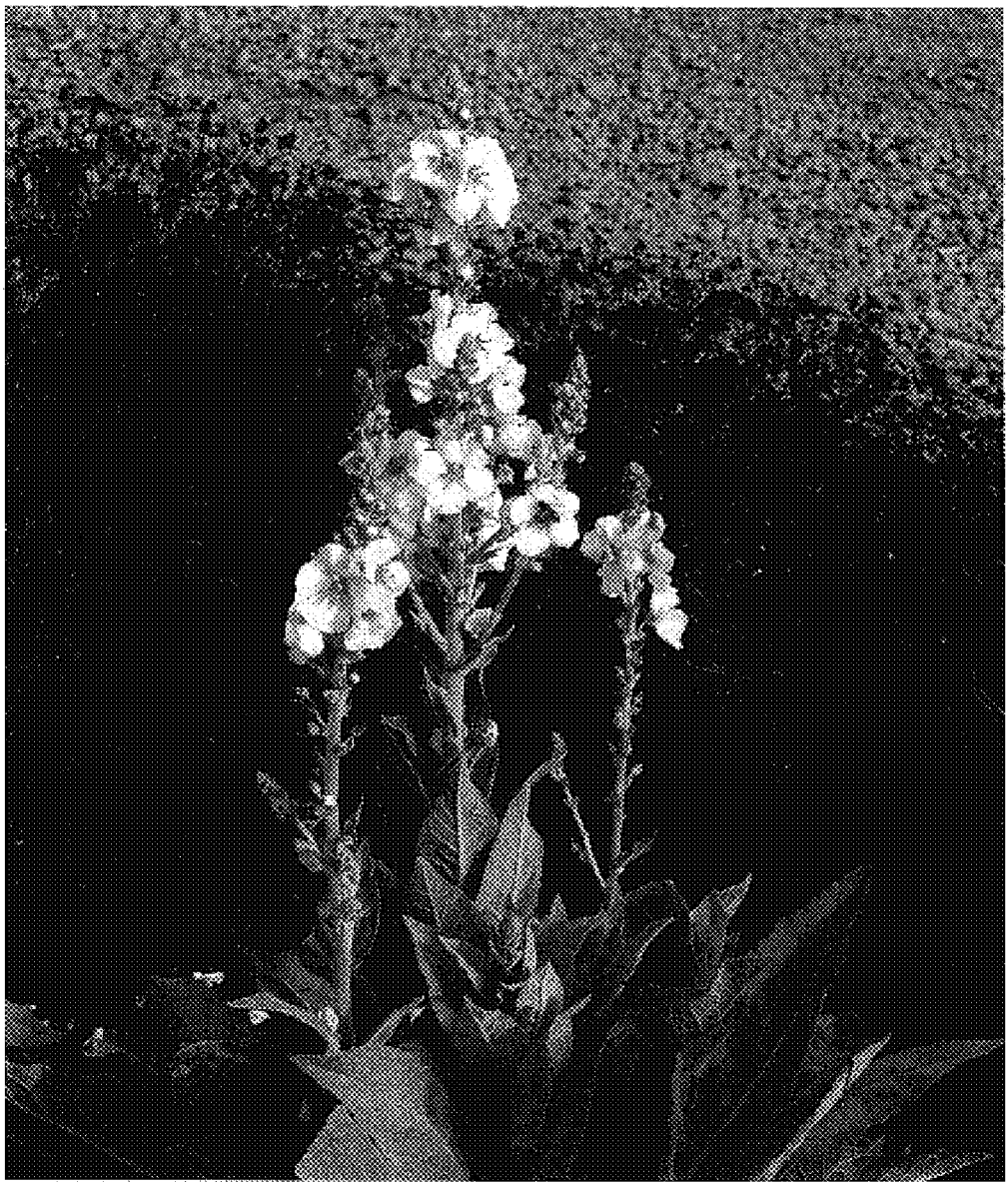

* * * * *